(12) United States Patent
Djupesland

(10) Patent No.: US 8,596,278 B2
(45) Date of Patent: *Dec. 3, 2013

(54) NASAL DEVICES

(75) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 2197 days.

This patent is subject to a terminal disclaimer.

(21) Appl. No.: 10/469,106

(22) PCT Filed: Feb. 26, 2002

(86) PCT No.: PCT/IB02/01522
§ 371 (c)(1),
(2), (4) Date: Feb. 6, 2004

(87) PCT Pub. No.: WO02/068029
PCT Pub. Date: Sep. 6, 2002

(65) Prior Publication Data
US 2004/0112379 A1    Jun. 17, 2004

Related U.S. Application Data

(63) Continuation-in-part of application No. 09/700,532, filed on Nov. 15, 2000, now Pat. No. 6,715,485.

(30) Foreign Application Priority Data

Feb. 26, 2001   (GB) .................................. 0104692.9

(51) Int. Cl.
*A61M 15/08*    (2006.01)
*A61M 16/00*    (2006.01)

(52) U.S. Cl.
USPC ............. 128/207.18; 128/200.24; 128/200.26

(58) Field of Classification Search
USPC ............ 128/200.11, 200.12, 200.13, 200.14, 128/203.12, 203.15, 203.18, 204.18, 207.18
See application file for complete search history.

(56) References Cited

U.S. PATENT DOCUMENTS

| | | | | |
|---|---|---|---|---|
| 3,730,179 A | * | 5/1973 | Williams | 128/204.18 |
| 4,817,626 A | * | 4/1989 | Blaine | 600/541 |
| 5,431,636 A | * | 7/1995 | Stangerup | 604/215 |
| 5,562,093 A | * | 10/1996 | Gerson | 128/203.11 |

(Continued)

FOREIGN PATENT DOCUMENTS

| | | |
|---|---|---|
| DE | 298 14 024 | 10/1998 |
| EP | 0 753 319 | 1/1997 |
| WO | 98/53869 | 12/1998 |
| WO | 00/51672 | 9/2000 |

OTHER PUBLICATIONS

U.S. Appl. No. 11/816,984, filed Aug. 23, 2007, Djupesland.
U.S. Appl. No. 12/161,466, filed Jul. 18, 2008, Djupesland.

(Continued)

*Primary Examiner* — Annette Dixon
(74) *Attorney, Agent, or Firm* — Lihua Zheng; Mary S. Consalvi; Proskauer Rose LLP

(57) ABSTRACT

A nasal delivery device for and a method of delivering a substance to a nasal cavity of a subject, the delivery device comprising: a delivery unit for delivering a flow entraining a substance to one nostril of a subject, the delivery unit including a nosepiece for fitting to a nostril of the subject; and a flow resistor unit for fitting to the other nostril of the subject, the flow resistor unit including a progressive resistor for progressively providing an increasing flow resistance to the delivered flow.

29 Claims, 13 Drawing Sheets

(56) References Cited

U.S. PATENT DOCUMENTS

| | | | |
|---|---|---|---|
| 5,727,546 A | 3/1998 | Clarke et al. | |
| 5,743,256 A * | 4/1998 | Jalowayski | 128/201.18 |
| 5,765,558 A * | 6/1998 | Psaros et al. | 128/207.14 |
| RE36,070 E * | 2/1999 | Ballini et al. | 128/200.14 |
| 5,950,631 A * | 9/1999 | Donaldson et al. | 128/898 |
| 6,273,084 B1 * | 8/2001 | Frid | 128/200.23 |
| 6,308,703 B1 * | 10/2001 | Alving et al. | 128/203.12 |
| 6,630,169 B1 * | 10/2003 | Bot et al. | 424/489 |
| 6,636,767 B1 * | 10/2003 | Knudson et al. | 607/42 |
| 6,715,485 B1 * | 4/2004 | Djupesland | 128/203.15 |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 8,146,589 B2 * | 4/2012 | Djupesland | 128/203.18 |
| 2004/0112378 A1 | 6/2004 | Djupesland | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0096589 A1 | 5/2006 | Djupesland | |
| 2006/0169278 A1 | 8/2006 | Djupesland | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland | |
| 2008/0223363 A1 | 9/2008 | Djupesland | |
| 2008/0289629 A1 | 11/2008 | Djupesland | |
| 2009/0101146 A1 | 4/2009 | Djupesland | |

OTHER PUBLICATIONS

U.S. Appl. No. 12/279,285, filed Aug. 13, 2008, Djupesland.
U.S. Appl. No. 12/279,291, filed Aug. 13, 2008, Djupesland.
U.S. Appl. No. 12/281,547, filed Sep. 3, 2008, Djupesland.
U.S. Appl. No. 12/281,894, filed Sep. 5, 2008, Djupesland.
U.S. Appl. No. 12/293,972, filed Sep. 22, 2008, Djupesland.
U.S. Appl. No. 12/298,292, filed Oct. 23, 2008, Djupesland.
U.S. Appl. No. 12/303,667, filed Dec. 5, 2008, Djupesland.
U.S. Appl. No. 12/375,115, filed Jan. 26, 2009, Djupesland.
U.S. Appl. No. 12/516,399, filed May 27, 2009, Djupesland.
U.S. Appl. No. 12/516,401, filed May 27, 2009, Djupesland.
U.S. Appl. No. 12/516,404, filed May 27, 2009, Djupesland.
U.S. Appl. No. 12/594,361, filed Oct. 2, 2009, Djupesland et al.
U.S. Appl. No. 12/594,365, filed Oct. 2, 2009, Djupesland et al.

* cited by examiner

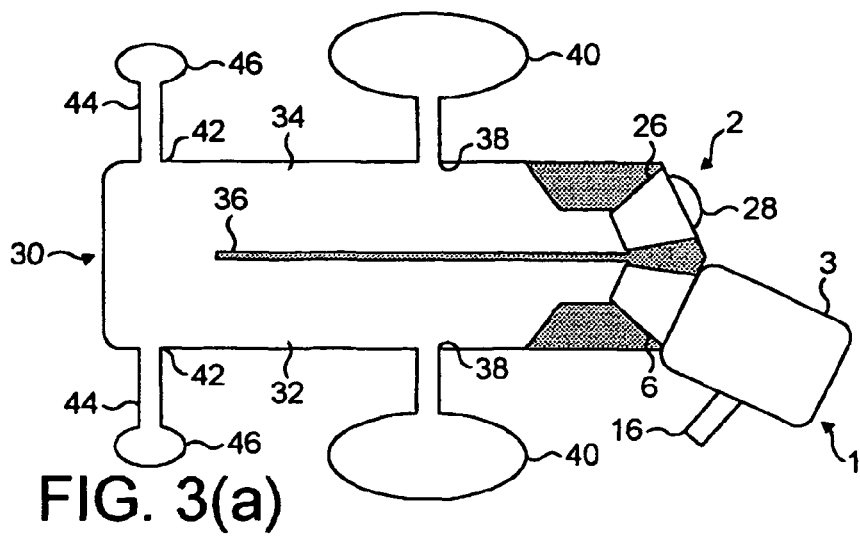
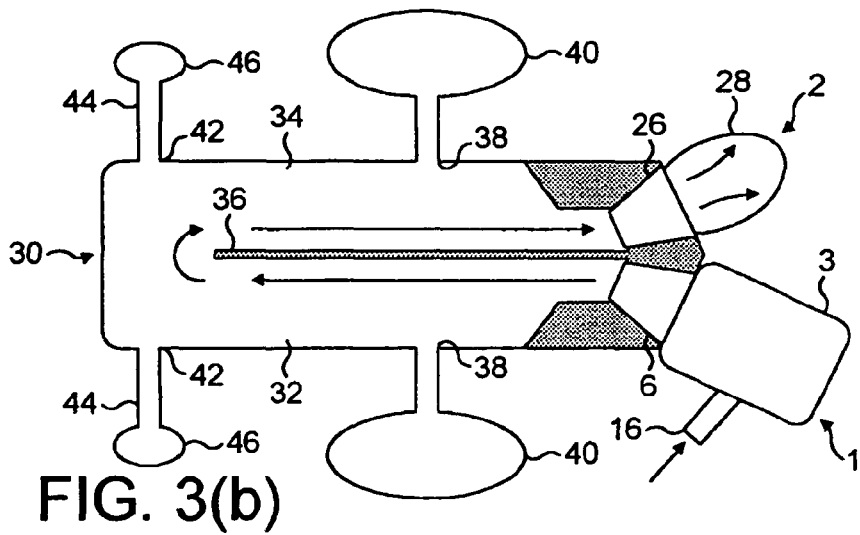
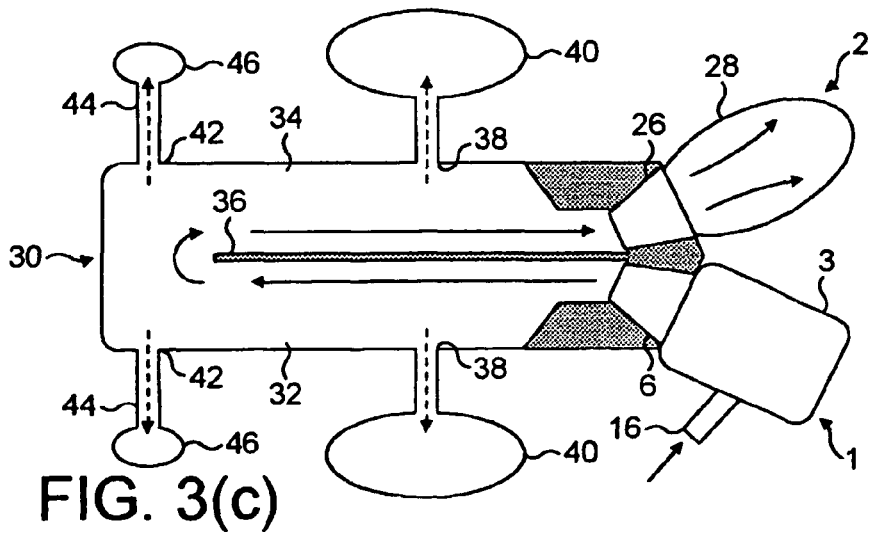

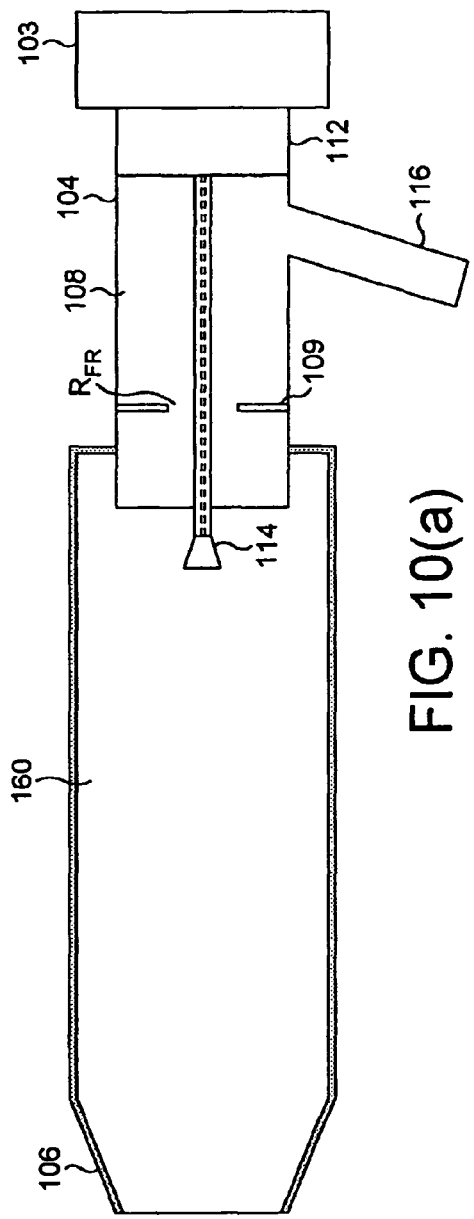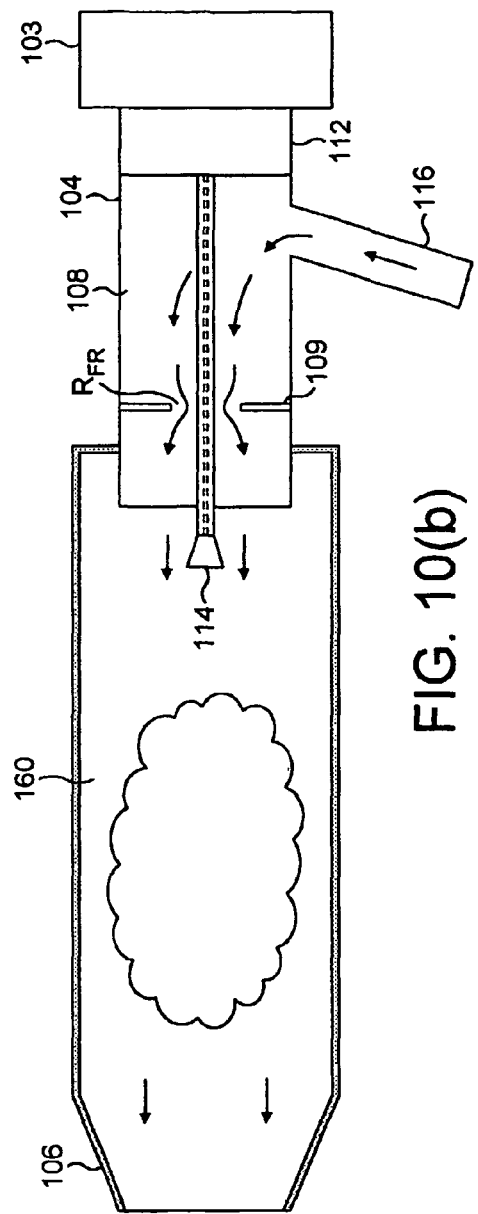
FIG. 10(a)
FIG. 10(b)

NASAL DEVICES

This application is a national phase of International Application No. PCT/IB02/01522 filed Feb. 26, 2002 and published in the English language, and a continuation-in-part of U.S. patent application Ser. No. 09/700,532 filed Nov. 15, 2000, which is hereby incorporated herein by reference in its entirety.

The present invention relates to a nasal delivery device for and a method of delivering a substance, in particular one of a liquid, as a suspension or solution, or a powder containing a medicament, especially systemic or topical pharmaceuticals, to the nasal airway of a subject.

BACKGROUND OF THE INVENTION

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisioned that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as helicobacter pylori infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

SUMMARY OF THE INVENTION

In one aspect the present invention provides a nasal delivery device for delivering a substance to a nasal cavity of a subject, comprising: a delivery unit for delivering a flow entraining a substance to one nostril of a subject, the delivery unit including a nosepiece for fitting to a nostril of the subject; and a flow resistor unit for fitting to the other nostril of the subject, the flow resistor unit including a progressive resistor for progressively providing an increasing flow resistance to the delivered flow.

In one embodiment the progressive resistor comprises an inflatable member which provides a progressively increasing resistance to the delivered flow.

In another embodiment the flow resistor unit includes a movable member which is movable under the action of a pressure developed in the nasal airway, and a biasing element for providing a progressively increasing resistance to the movement of the movable member.

Preferably, the flow resistor unit further includes a housing in which the movable member is movable, the housing including an aperture therein which is located such as to vent the housing when movable member is driven a predeterminable distance corresponding to a first predeterminable pressure, whereby the flow resistance decreases and the flow rate increases following the development of a second predeterminable pressure.

Preferably, the flow resistor unit includes a filter for collecting any vented material.

Preferably, the delivery unit includes a substance supply unit which is actuatable to supply a substance.

More preferably, the substance supply unit is actuatable by the progressive flow resistor unit.

In one embodiment the substance supply unit is configured to be actuated to supply a substance at a predeterminable pressure.

In another embodiment the substance supply unit is configured to be actuated to supply a substance at a predeterminable flow rate.

In a further embodiment the substance supply unit is configured to be actuated to supply a substance at one or both of a predeterminable pressure and a predeterminable flow rate.

Preferably, the delivery unit further includes a mouthpiece through which the subject in use exhales.

In one embodiment the delivery unit further includes a flow channel fluidly connecting the nosepiece and the mouthpiece, whereby exhaled air from an exhalation breath is delivered through the nosepiece.

In another embodiment the delivery unit further includes a flow channel fluidly connected to the nosepiece through which a gas flow, separate to an exhaled air flow from an exhalation breath of a subject, is in use delivered, and a gas supply unit for supplying a gas flow to the flow channel.

Preferably, the substance supply unit includes a dosing unit for supplying a substance.

In one embodiment the dosing unit comprises a nebulizer for supplying an aerosol.

In another embodiment the dosing unit comprises an aerosol canister for supplying an aerosol.

In a further embodiment the dosing unit comprises a delivery pump unit for supplying an aerosol.

In one preferred embodiment the dosing unit comprises a liquid pump unit for supplying a liquid aerosol.

In another preferred embodiment the dosing unit comprises a powder pump unit for supplying a powder aerosol.

In a yet further embodiment the dosing unit comprises a powder delivery unit for delivering a powder aerosol.

In another aspect the present invention provides a nasal delivery device for delivering a flow entraining a substance to a nostril of a subject, including: a nosepiece for fitting to a nostril of a subject; and a flow resistor upstream of the outlet of the nosepiece to provide a predeterminable flow resistance to the delivered flow.

In one embodiment the flow resistor is a progressive resistor for progressively providing an increasing flow resistance to the delivered flow.

In another embodiment the flow resistor is a fixed resistor for providing a predeterminable resistance to the delivered flow.

Preferably, the delivery device further includes: a substance supply unit which is actuatable to supply a substance.

In one embodiment the substance supply unit is configured to be actuated to supply a substance at a predeterminable pressure.

In another embodiment the substance supply unit is configured to be actuated to supply a substance at a predeterminable flow rate.

In a further embodiment the substance supply unit is configured to be actuated to supply a substance at one or both of a predeterminable pressure and a predeterminable flow rate.

Preferably, the delivery device further includes: a mouthpiece through which the subject in use exhales.

In one embodiment the delivery device further includes: a flow channel fluidly connecting the nosepiece and the mouthpiece, whereby exhaled air from an exhalation breath is delivered through the nosepiece.

In another embodiment the delivery device further includes: a flow channel fluidly connected to the nosepiece through which a gas flow, separate to an exhaled air flow from an exhalation breath of a subject, is in use delivered; and a gas supply unit for supplying a gas flow to the flow channel.

Preferably, the substance supply unit includes a dosing unit for supplying a substance.

In one embodiment the dosing unit comprises a nebulizer for supplying an aerosol.

In another embodiment the dosing unit comprises an aerosol canister for supplying an aerosol.

In a further embodiment the dosing unit comprises a delivery pump unit for supplying an aerosol.

In one preferred embodiment the dosing unit comprises a liquid pump unit for supplying a liquid aerosol.

In another preferred embodiment the dosing unit comprises a powder pump unit for supplying a powder aerosol.

In a yet further embodiment the dosing unit comprises a powder delivery unit for delivering a powder aerosol.

In a further aspect the present invention provides a method of delivering a substance to a nasal cavity of a subject, comprising the steps of: delivering a flow entraining a substance to one nostril of a subject; and progressively providing an increasing flow resistance to the delivered flow.

Preferably, the method further comprises the step of: decreasing the flow resistance on development of a predeterminable pressure.

In a yet further aspect the present invention provides a method of delivering a flow entraining a substance to a nostril of a subject, comprising the steps of: delivering a flow entraining a substance to a nostril of a subject; and providing a predeterminable flow resistance to the delivered flow.

In one embodiment the step of providing a predeterminable flow resistance to the delivered flow comprises the step of: progressively providing an increasing flow resistance to the delivered flow.

In another embodiment the step of providing a predeterminable flow resistance to the delivered flow comprises the step of: providing a predeterminable resistance to the delivered flow.

BRIEF DESCRIPTION OF THE DRAWINGS

Preferred embodiments of the present invention will now be described hereinbelow by way of example only with reference to the accompanying drawings, in which:

FIG. 3(a) illustrates the delivery unit and the flow resistor unit of the nasal delivery device of the first embodiment of the present invention fitted to the respective nostrils of a subject, where the subject is not exhaling through the mouthpiece of the delivery unit;

FIG. 3(b) illustrates the delivery unit and the flow resistor unit of the nasal delivery device of the first embodiment of the present invention fitted to the respective nostrils of a subject, where the subject has commenced exhaling through the mouthpiece of the delivery unit and the pressure developed in the nasal airway is at the actuation pressure of the delivery unit;

FIG. 3(c) illustrates the delivery unit and the flow resistor unit of the nasal delivery device of the first embodiment of the present invention fitted to the respective nostrils of a subject, where the delivery unit has been actuated and the subject is continuing to exhale through the mouthpiece of the delivery unit such as to develop an increased pressure in the nasal airway;

FIG. 10(a) schematically illustrates a nasal delivery device in accordance with a sixth embodiment of the present invention;

FIG. 10(b) illustrates the nasal delivery device of FIG. 10(a) in the actuated configuration;

DETAILED DESCRIPTION OF THE INVENTION

Figure 1A:
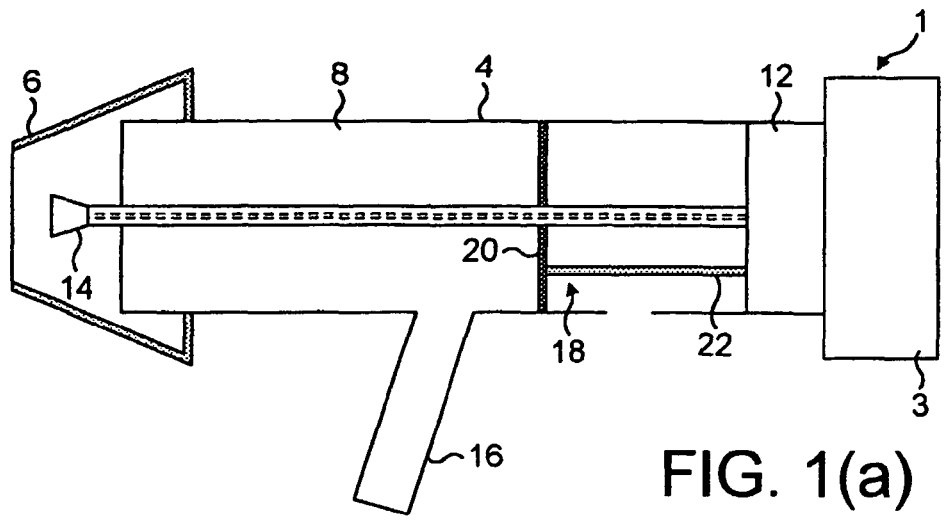
FIG. 1(a) schematically illustrates the delivery unit of a nasal delivery device in accordance with a first embodiment of the present invention.
Figure 1B:
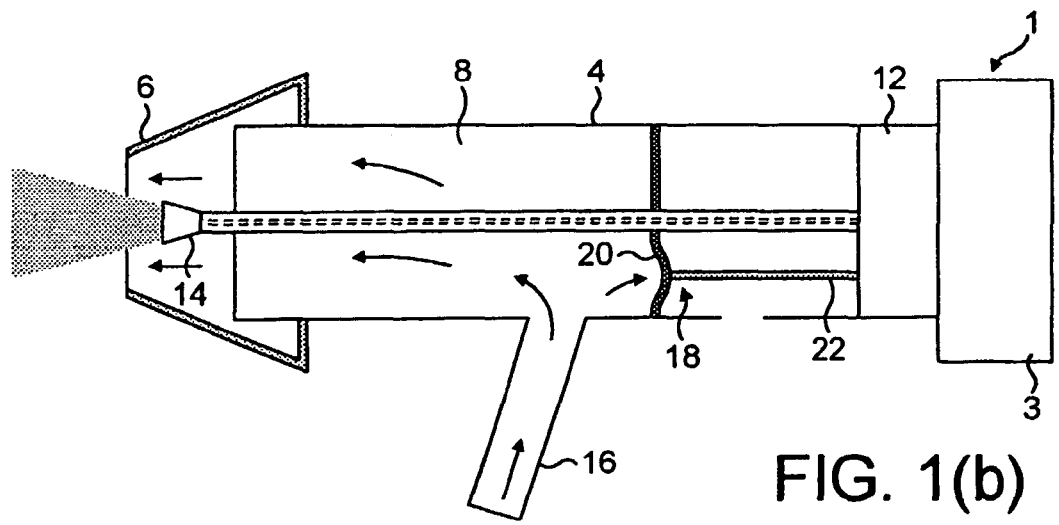
FIG. 1(b) illustrates the nasal delivery device of FIG. 1(a) in the actuated configuration.
Figure 2A:
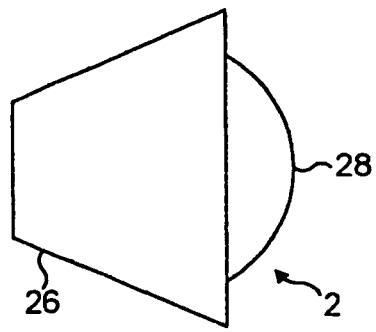
FIG. 2(a) illustrates the flow resistor unit of the nasal delivery device of the first embodiment of the present invention.
Figure 2B:
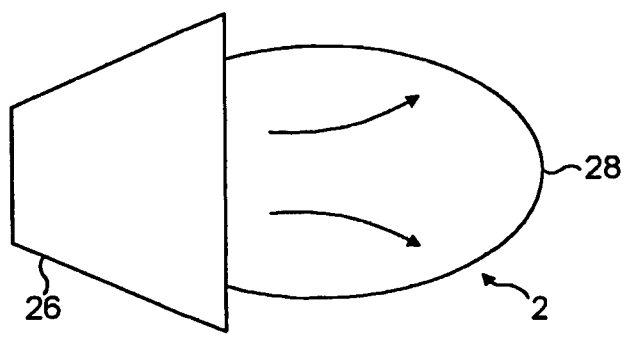
FIG. 2(b) illustrates the flow resistor unit of FIG. 2(a) in which the flow resistor thereof is partially inflated at a pressure corresponding to the actuation pressure of the delivery unit.
Figure 2C:
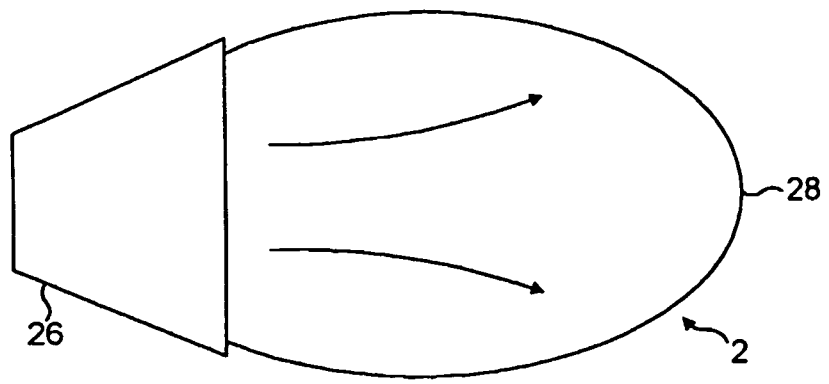
FIG. 2(c) illustrates the flow resistor unit of FIG. 2(a) in which the flow resistor thereof is inflated at an increased pressure greater than the actuation pressure of the delivery unit.

FIGS. 1 and 2 illustrate respectively a delivery unit 1 and a flow resistor unit 2 of a nasal delivery device in accordance with a first embodiment of the present invention.

The delivery unit 1 comprises a housing 3 which includes a tubular member 4, in this embodiment a cylindrical member, and a nosepiece 6 for fitting in one nostril of a subject which is disposed to one, the distal, end of the tubular member 4.

The tubular member 4 includes a cavity 8 at the one end thereof which is in fluid communication with the nosepiece 6 such that exhalation breath introduced thereinto is directed through the nosepiece 6.

The delivery unit 1 further comprises a substance supply unit 12 for delivering metered doses of a substance, in this embodiment an aerosol canister for delivering metered volumes of a propellant, preferably a hydrofluoroalkane (HFA) propellant or the like, containing medicament, either as a suspension or solution. In this embodiment the substance supply unit 12 is configured to deliver substance which comprises a relatively large fraction of small particles.

The substance supply unit 12 is primeable, in this embodiment by loading a biasing element, and includes a release mechanism which, when triggered, releases the biasing element and actuates the substance supply unit 12 to deliver a metered dose of a substance.

In an alternative embodiment the substance supply unit 12 could comprise a mechanical delivery pump, in particular a liquid delivery pump or a powder delivery pump, which delivers metered doses of a substance on actuation thereof.

In another alternative embodiment the substance supply unit 12 could comprise a dry powder delivery unit which delivers metered doses of a substance, as a dry powder, on actuation thereof.

In yet another alternative embodiment the substance supply unit 12 could comprise a nebulizer which delivers metered doses of a substance, as an aerosol spray, on actuation thereof.

The delivery unit 1 further comprises a nozzle 14 which is fluidly connected to the substance supply unit 12 for providing an aerosol spray through the nosepiece 6. In this embodiment the nozzle 14 is disposed in the nosepiece 6 co-axially with the same.

The housing 3 further includes a mouthpiece 16 which is in fluid communication with the chamber 8 in the tubular member 4 and through which a subject exhales to actuate the substance supply unit 12, as will be described in more detail hereinbelow.

The delivery unit 1 further comprises a trigger mechanism 18 which is configured as to be actuatable to cause actuation of the substance supply unit 12 on the generation of a predetermined actuation pressure within the chamber 8 in the tubular member 4.

The trigger mechanism 18 includes a flexible member 20, in this embodiment a resilient membrane, which defines a part of the wall of the chamber 8 in the tubular member 4, and a link 22 which couples the flexible member 20 and the release mechanism of the substance supply unit 12. The flexible member 40 is configured such as, on generation of a predetermined actuation pressure within the chamber 8 in the tubular member 4, to be deflected sufficiently as to actuate the release mechanism of the substance supply unit 12 and deliver a metered dose of a substance (as illustrated in FIG. 1(*b*)).

The flow resistor unit 2 comprises a nosepiece 26 for fitting in the other nostril of the subject and a progressive flow resistor 28 in fluid communication therewith.

The progressive flow resistor 28, in this embodiment a balloon, provides a progressively increasing resistance to the exhaled air flow from the exhalation breath of a subject. FIGS. 2(*a*) to (*c*) illustrate respectively the progressive flow resistor 28 when not inflated, inflated at the actuation pressure of the delivery unit 1, and inflated at a pressure in excess of the actuation pressure of the delivery unit 1. In this embodiment the progressive flow resistor 28 also acts as an indicator for providing an indication as to operation of the delivery device.

Operation of the delivery device will now be described hereinbelow with reference to FIGS. 3(*a*) to (*c*), which drawings diagrammatically illustrate the nasal airway 30 of a human subject. The nasal airway 30 comprises the two nasal cavities 32, 34 separated by the nasal septum 36, which airway 30 includes numerous ostia, such as the paranasal sinus ostia 38 connected to the paranasal sinuses 40 and the tubal ostia 42 connected to the tuba auditiva 44 and the middle ears 46, and olfactory cells, and is lined by the nasal mucosa.

Firstly, the delivery unit 1 is inserted in one nostril of a subject and the flow resistor unit 2 is inserted in the other nostril of the subject.

The subject then begins to exhale through the mouthpiece 16 of the delivery unit 1, which exhalation acts to close the oropharyngeal velum of the subject and increase the pressure in the nasal airway 30 by the introduction of exhaled air from the exhalation breath thereinto, with the progressive flow resistor 28 providing an increased resistance to the exhaled air flow. The pressure in the nasal airway 30 increases rapidly until the actuation pressure of the delivery unit 1 is reached, at which point the substance supply unit 12 of the delivery unit 1 is actuated to deliver a metered dose of a substance to the nasal airway 30. The actuation pressure of the delivery unit 1 is less than that normally required to open the ostia in the nasal airway 30, notably the paranasal sinus ostia 38 and the tubal ostia 42. In this embodiment the delivery rate from the substance supply unit 12 is low such that the airborne particles are resident in the nasal airway 30 for a long period of time.

The subject continues to exhale through the mouthpiece 16 of the delivery unit 1, with the progressive flow resistor 28 providing an increasing resistance to the exhaled air flow, in this embodiment by inflation of the balloon. The pressure in the nasal airway 30 increases until the opening pressure for the paranasal sinus ostia 38 and the tubal ostia 42 is reached, at which point substance is driven into the paranasal sinuses 40 and the tuba auditiva 44 and the middle ears 46. In this embodiment the nasal airway 30 acts as a spacer for containing small airborne particles having an optimal particle size, typically in the range of from about 1 μm to about 10 μm for penetration into the paranasal sinuses 40 and the tuba auditiva 44 and the middle ears 46.

By using a progressive exit resistor, the pressure will gradually build up until the opening pressure is reached. This pressure is typically from about 0 to about 140 cmH$_2$O ($\approx$0-1.4 kPa) in normal subjects. In one study of subjects with impaired tubal function and middle ear pathology, half had an opening pressure in this range, while the remaining subjects needed a higher pressure or could not open the tuba auditiva. In another study, a pressure of form about 100 to about 200 cmH$_2$O ($\approx$1 to 2 kPa) was required to flush air through the tuba auditiva.

In this embodiment the speed of the delivered aerosol is slowed significantly as compared, for example, to conventional pMDIs, allowing for a greater uptake of substance. A significant problem with conventional pMDIs is the high release speed of the aerosol. This high speed is disadvantageous not only for inhalation to the lungs, but also nasal delivery. The reason is that the aerosol particles are shot against the nasal mucosa which leads to increased deposition in the mouth and the anterior regions of the nasal cavities. A soft mist inhaler using mechanical energy to produce small particles reduces the speed of the delivered particles by a factor of five.

In this embodiment the optimal mean particle size is between about 10 μm and about 30 μm. pMDIs generally produce smaller particles, but the particle size can be increased by one or both of reducing the driving pressure in the pMDI and modifying the dimensions of the nozzle 14. Traditional spray pumps normally produce particles with a mean particle size of from about 50 μM to about 60 μm, but simple modification allows mean particle sizes of from about 25 μm to about 30 μm to be generated. Specialized mechanical pumps can generate aerosol mists with mean particle sizes down to 5 μm (NebuHaler, Boehringer Ingelheim). A nebulizer is also available (PARI) for the generation of aerosol mists which have a mean particle size of about 10 μm.

Figure 4A:
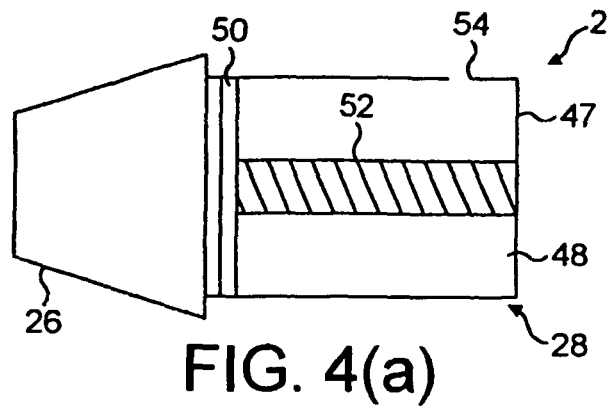
FIG. 4(a) illustrates the flow resistor unit of a nasal delivery device in accordance with a second embodiment of the present invention.
Figure 4B:
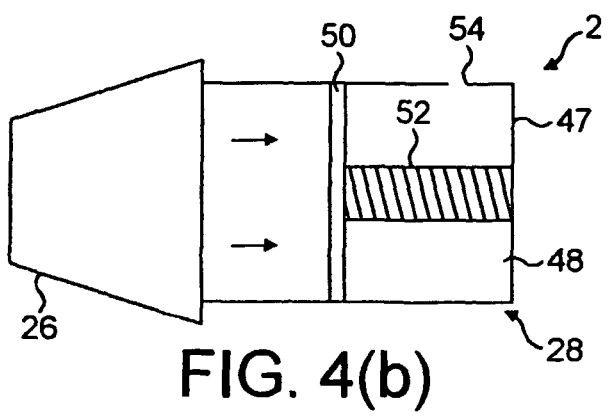
FIG. 4(b) illustrates the flow resistor unit of FIG. 4(a) in which the progressive flow resistor thereof is partially driven at a pressure corresponding to the actuation pressure of the delivery unit.
Figure 4C:
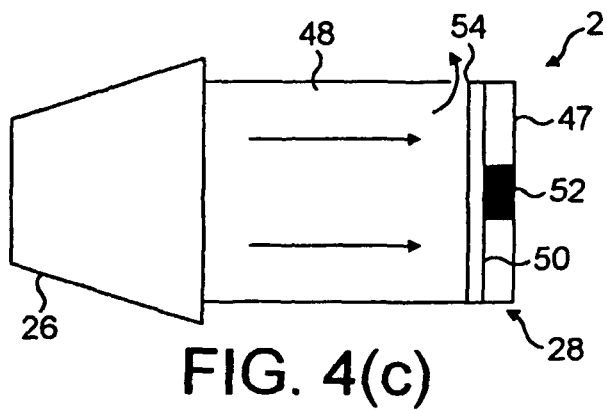
FIG. 4(c) illustrates the flow resistor unit of FIG. 4(a) in which the progressive flow resistor thereof is driven at an increased pressure greater than the actuation pressure of the delivery unit.

FIG. 4 illustrates the flow resistor unit 2 of a delivery device in accordance with a second embodiment of the present invention. The delivery unit 1 is of the same construction as the delivery unit 1 of the delivery device of the above-described first embodiment.

The flow resistor unit 2 comprises a nosepiece 26 for fitting in the other nostril of the subject and a progressive flow resistor 28 in fluid communication therewith.

The progressive flow resistor 28 provides a progressively increasing resistance to the exhaled air from the exhalation breath of a subject. FIGS. 4(*a*) to (*c*) illustrate respectively the progressive flow resistor 28 where the subject is not exhaling, the pressure in the nasal airway 30 is at the actuation pressure of the delivery unit 1, and the pressure in the nasal airway is at a pressure in excess of the actuation pressure of the delivery unit 1. In this embodiment the progressive flow resistor 28 also acts as an indicator for providing an indication as to the operation of the delivery device.

The progressive flow resistor 28 comprises a housing 47 which defines a chamber 48 which is in fluid communication with the nosepiece 26, a piston member 50 which is slideable in the chamber 48 under the action of the pressure developed in the nasal airway 30, and a biasing element 52, in this embodiment a resilient element, in particular a compression spring, for providing a progressively increasing resistance to the movement of the piston member 50.

In this embodiment the housing 47 includes an aperture 54 therein which is located such as to provide a vent to the atmosphere when the piston member 50 is driven a predetermined distance through the chamber 48 which corresponds to a pressure which exceeds the opening pressure for the paranasal sinus ostia 38 and the tubal ostia 42. With this configuration, the flow resistance gradually decreases and the air flow increases following the development of a pressure exceeding the opening pressure for the paranasal sinus ostia 38 and the tubal ostia 42. This pressure and flow regime promotes the deposition of airborne particles in the nasal airway 30. Furthermore, this pressure and flow regime ensures that airborne particles are flushed out of the nasal airway before the procedure is terminated, thereby preventing airborne particles, which could subsequently be inhaled, from remaining in the nasal airway 30.

In a preferred embodiment the progressive flow resistor 28 can comprise a filter for collecting any vented substance.

Figure 5A:
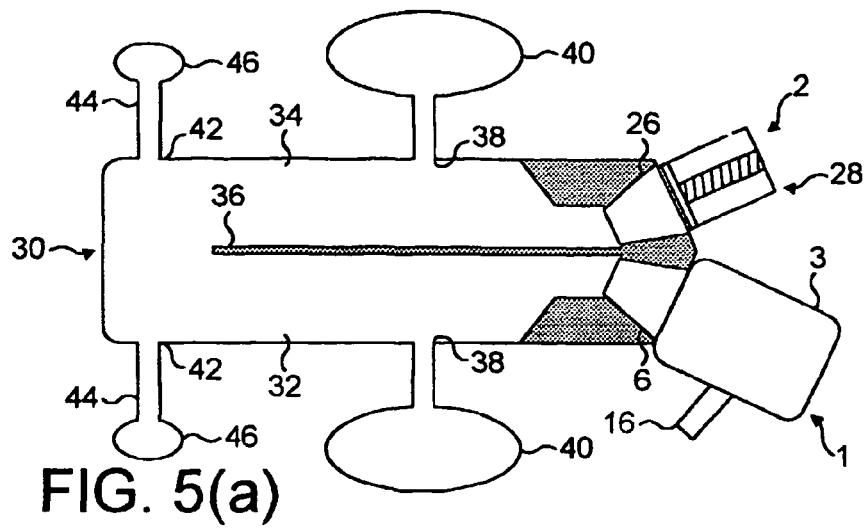
FIG. 5(a) illustrates the delivery unit and the flow resistor unit of the nasal delivery device of the second embodiment of the present invention fitted to the respective nostrils of a subject, where the subject is not exhaling through the mouthpiece of the delivery unit.
Figure 5B:
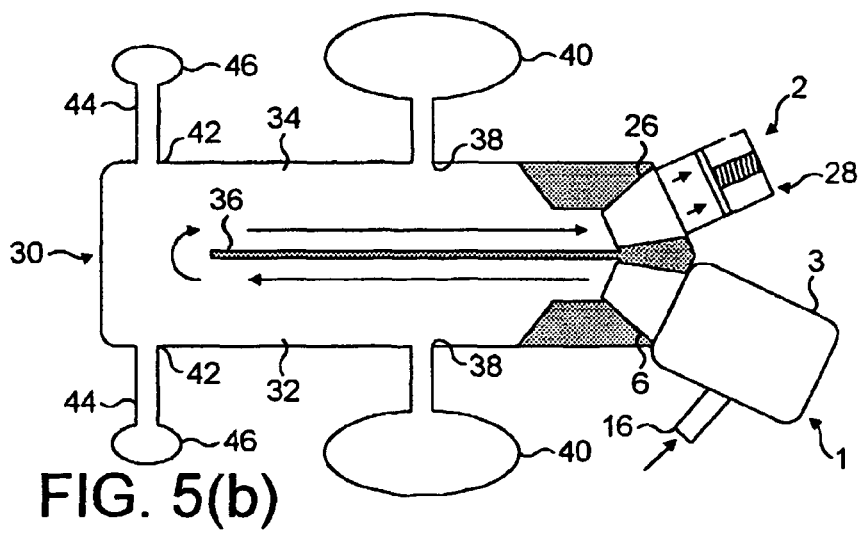
FIG. 5(b) illustrates the delivery unit and the flow resistor unit of the nasal delivery device of the second embodiment of the present invention fitted to the respective nostrils of a subject, where the subject has commenced exhaling through the mouthpiece of the delivery unit and the pressure developed in the nasal airway is at the actuation pressure of the delivery unit.
Figure 5C:
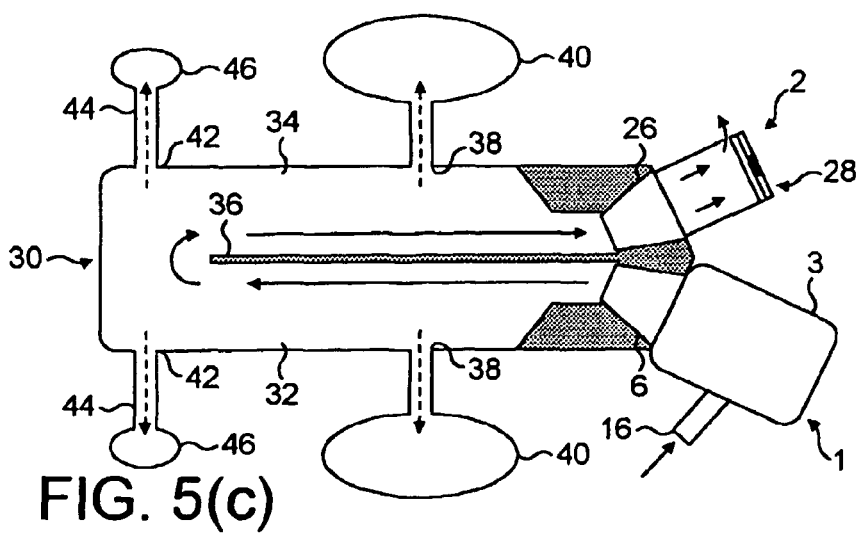
FIG. 5(c) illustrates the delivery unit and the flow resistor unit of the nasal delivery device of the second embodiment of the present invention fitted to the respective nostrils of a subject, where the delivery unit has been actuated and the subject is continuing to exhale through the mouthpiece of the delivery unit such as to develop an increased pressure in the nasal airway.

Operation of the delivery device will now be described hereinbelow with reference to FIGS. 5(*a*) to (*c*). Operation of the delivery device is the same as for the above-described first embodiment, with the biasing element 52 providing a progressively increasing resistance to the movement of piston member 50, and the aperture 54 in the housing 47 venting exhaled air from the exhalation breath of a subject to the atmosphere when the piston member 50 is driven a predetermined distance through the chamber 48 which corresponds to a pressure which exceeds the opening pressure for the paranasal sinus ostia 38 and the tubal ostia 4, whereby the flow resistance in the nasal airway 30 gradually decreases and the air flow increases following the development of a pressure exceeding the opening pressure for the paranasal sinus ostia 38 and the tubal ostia 42.

Figure 6A:
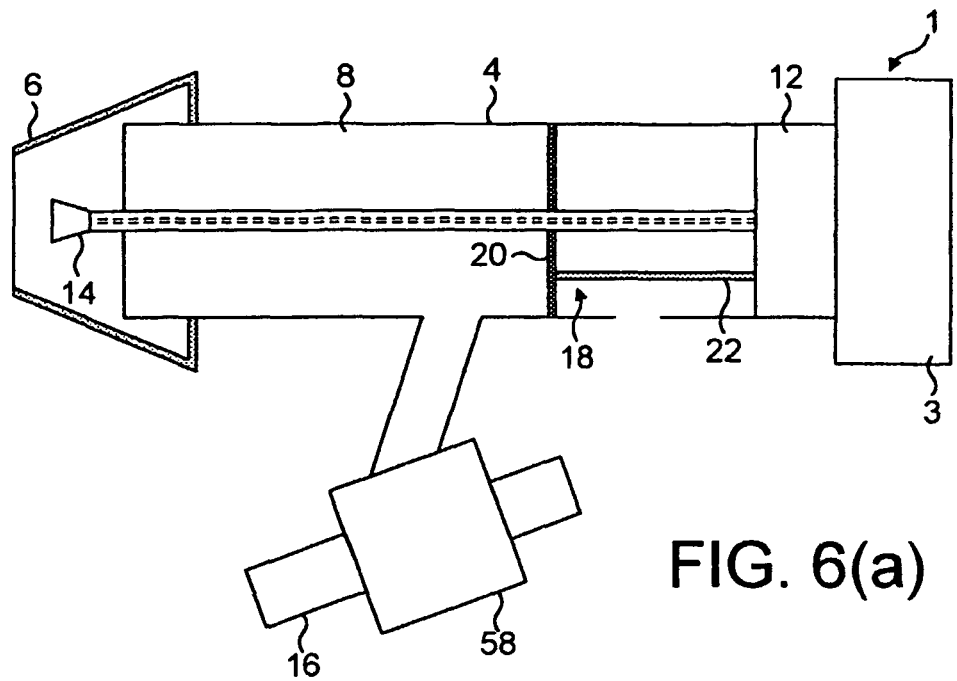
FIG. 6(a) schematically illustrates the delivery unit of a nasal delivery device in accordance with a third embodiment of the present invention.
Figure 6B:
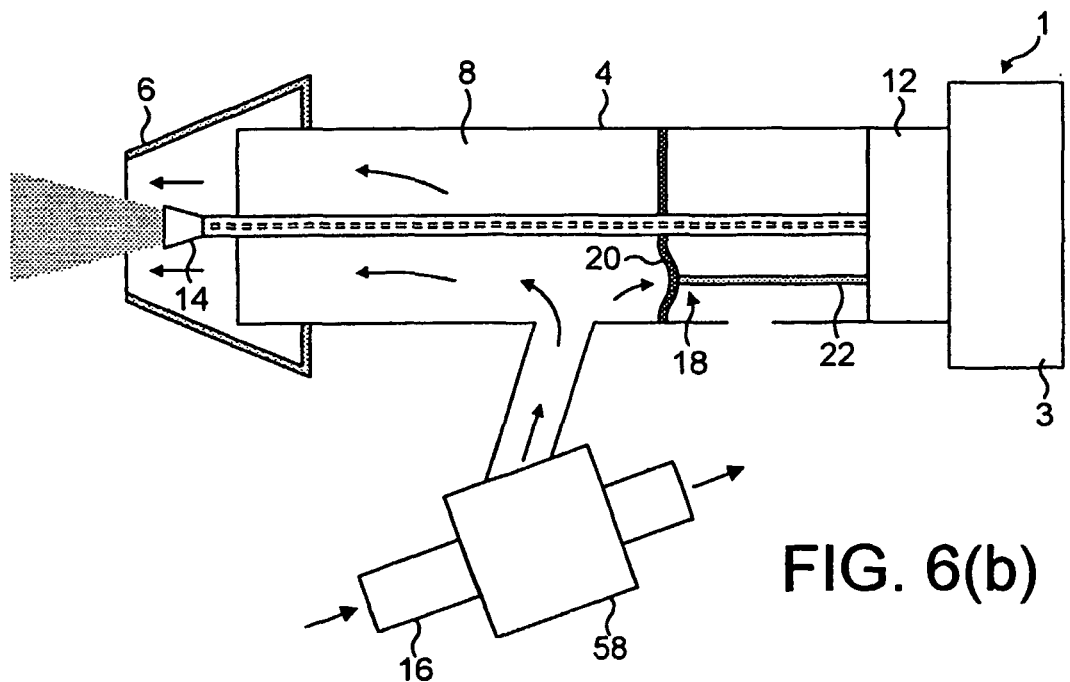
FIG. 6(b) illustrates the nasal delivery device of FIG. 6(a) in the actuated configuration.

FIG. 6 illustrates the delivery unit 1 of a delivery device in accordance with a third embodiment of the present invention. The flow resistor unit 2 is of the same construction as the flow resistor unit 2 of the delivery device of the above-described first embodiment.

The delivery unit 1 of this embodiment is very similar to the delivery unit 1 of the above-described first embodiment, and thus, in order to avoid unnecessary duplication of description, only the differences will be described in detail, with like reference signs designating like parts The delivery unit 1 of this embodiment differs from that of the above-described first embodiment in further comprising an exhalation breath actuatable gas delivery unit 58 for delivering a gas flow to the chamber 8 in the housing 4 in response to exhalation by a subject, and in that the mouthpiece 16 is in fluid communication with the gas delivery unit 58 and not the chamber 8 in the housing 4, whereby a gas flow is delivered to the chamber 8 in the housing 4, and hence the nasal airway 30, in response to exhalation through the mouthpiece 16.

Operation of the delivery device is the same as for the above-described first embodiment, with a gas flow being delivered to the chamber 8 in the housing 4, and hence a pressure being developed in the nasal airway 30, in response to exhalation through the mouthpiece 16.

Figure 7A:
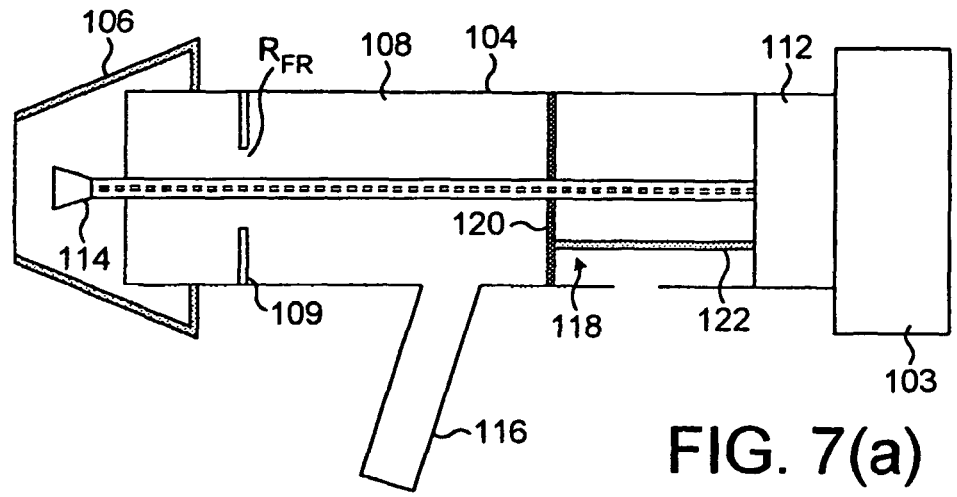
FIG. 7(a) schematically illustrates the delivery unit of a nasal delivery device in accordance with a fourth embodiment of the present invention.

FIGS. 7(*a*) and (*b*) illustrate a nasal delivery device in accordance with a fourth embodiment of the present invention.

The delivery device comprises a housing 103 which includes a tubular member 104, in this embodiment a cylindrical member, and a nosepiece 106 for fitting in one nostril of a subject which is disposed to one, the distal, end of the tubular member 104.

The tubular member 104 includes a chamber 108 at the one end thereof which is in fluid communication with the nosepiece 106 such that exhalation breath introduced thereinto is directed through the nosepiece 106.

The chamber 108 includes a flow resistor 109 which acts to restrict flow and thereby provide a flow resistance to an air flow driven through the chamber 198. In this embodiment the flow resistor 109 comprises a baffle which has a fixed flow resistance. With this configuration, the flow resistor 109 can be configured to provide the flow-limiting resistance, where this resistance is greater than the total nasal resistance, in the flow path through the delivery device and the nasal airway of the subject, and thereby provide for a maximum predetermined flow rate at the actuation pressure of the delivery device.

The delivery device further comprises a substance supply unit 112 for delivering metered doses of a substance, in this embodiment an aerosol canister for delivering metered volumes of a propellant, preferably a hydrofluoroalkane (HFA) propellant or the like, containing medicament, either as a suspension or solution. In this embodiment the substance supply unit 112 is configured to deliver substance which comprises a relatively large fraction of small particles.

The substance supply unit 112 is primeable, in this embodiment by loading a biasing element, and includes a release mechanism which, when triggered, releases the biasing element and actuates the substance supply unit 112 to deliver a metered dose of a substance.

In an alternative embodiment the substance supply unit 112 could comprise a mechanical delivery pump unit, in particular a liquid delivery unit or a powder delivery unit, which delivers metered doses of a substance on actuation thereof.

In another alternative embodiment the substance supply unit 112 could comprise a dry powder delivery unit which delivers metered doses of a substance, as a dry powder, on actuation thereof.

In yet another alternative embodiment the substance supply unit 112 could comprise a nebulizer which delivers metered doses of a substance, as an aerosol spray, on actuation thereof.

The delivery device further comprises a nozzle 114 which is fluidly connected to the substance supply unit 112 for providing an aerosol spray through the nosepiece 106. In this embodiment the nozzle 114 is disposed in the nosepiece 106 co-axially with the same.

The housing 103 further includes a mouthpiece 116 which is in fluid communication with the chamber 108 in the tubular member 104 and through which a subject exhales to actuate the substance supply unit 112, as will be described in more detail hereinbelow.

The delivery device further comprises a trigger mechanism 118 which is configured as to be actuatable to cause actuation of the substance supply unit 112 on the generation of a predetermined actuation pressure within the chamber 108 in the tubular member 104, and hence the nasal airway of the subject.

Figure 7B:
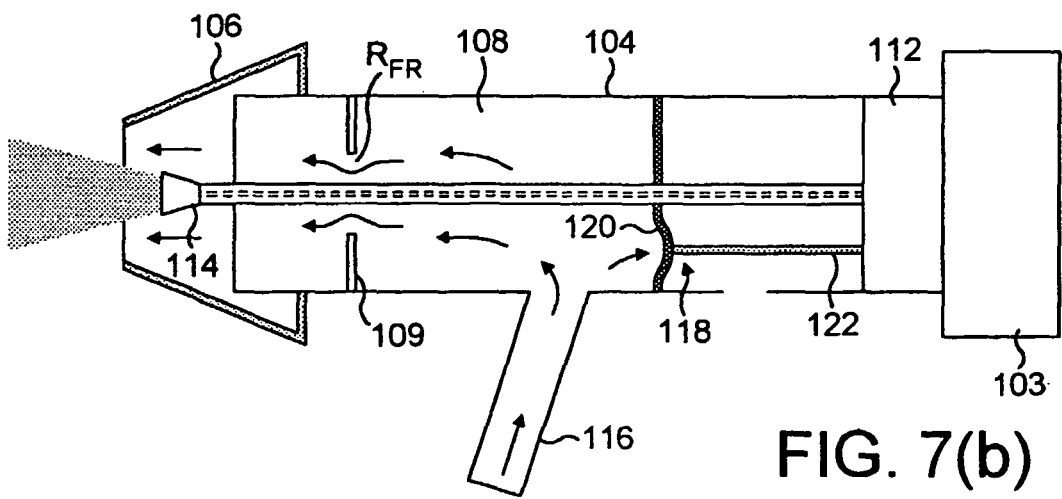
FIG. 7(b) illustrates the nasal delivery device of FIG. 7(a) in the actuated configuration.

The trigger mechanism 118 includes a flexible member 120, in this embodiment a resilient membrane, which defines a part of the wall of the chamber 108 in the tubular member 104, and a link 122 which couples the flexible member 120 and the release mechanism of the substance supply unit 112. The flexible member 120 is configured such as, on generation of a predetermined actuation pressure within the chamber 108 in the tubular member 104, to be deflected sufficiently as to actuate the release mechanism of the substance supply unit 112 and deliver a metered dose of a substance (as illustrated in FIG. 7(b)).

Figure 8A:
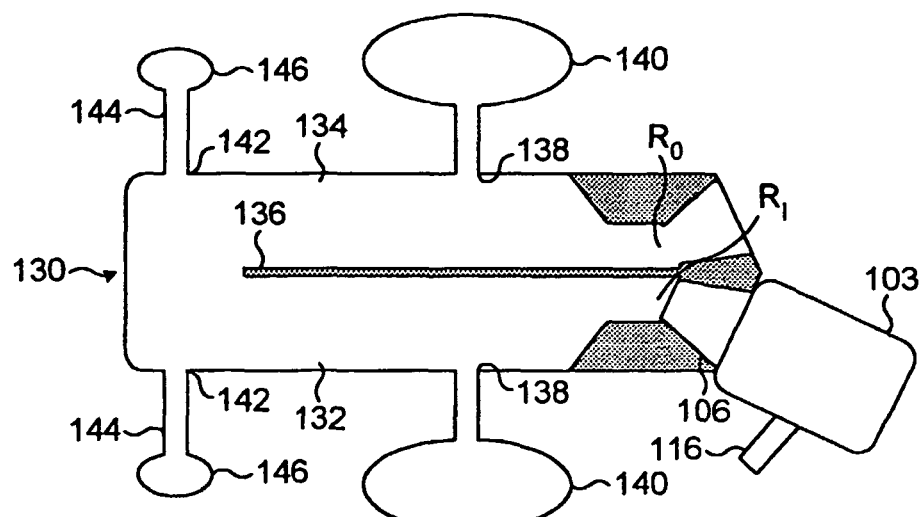
FIG. 8(a) illustrates the nasal delivery device of the fourth embodiment of the present invention fitted to a nostril of a subject, where the subject is not exhaling through the mouthpiece of the delivery unit.
Figure 8B:
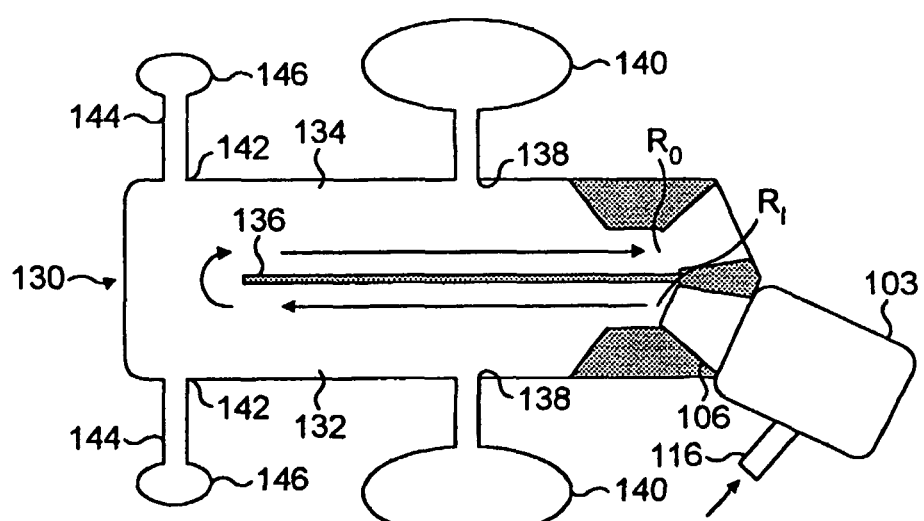
FIG. 8(b) illustrates the nasal delivery device of the fourth embodiment of the present invention fitted to a nostrils of a subject, where the delivery device has been actuated and the subject is continuing to exhale through the mouthpiece of the delivery device.

Operation of the delivery device will now be described hereinbelow with reference to FIGS. 8(a) and (b), which drawings diagrammatically illustrate the nasal airway 130 of a human subject. The nasal airway 130 comprises the two nasal cavities 132, 134 separated by the nasal septum 136, which airway 130 includes numerous ostia, such as the paranasal sinus ostia 138 connected to the paranasal sinuses 140 and the tubal ostia 142 connected to the tuba auditiva 144 and the middle ears 146, and olfactory cells, and is lined by the nasal mucosa.

Firstly, the nosepiece 106 of the delivery device is inserted in one nostril of a subject. The subject then begins to exhale through the mouthpiece 16, which exhalation acts to close the oropharyngeal velum of the subject and increase the pressure in the nasal airway 130 by the introduction of exhaled air from the exhalation breath thereinto, with the flow resistor 109 providing a fixed resistance to the exhaled air flow, and thereby providing for a predetermined flow rate from the delivery device. The pressure in the nasal airway 130 increases rapidly until the actuation pressure of the delivery device is reached, at which point the substance supply unit 112 is actuated to deliver a metered dose of a substance to the nasal airway 130. By the provision of the flow resistor 109 which has a flow resistance $R_{FR}$ greater than the combined flow resistances of the inlet and outlet flow resistances $R_I$, $R_O$, the flow rate through the nasal airway 130 is advantageously at a predetermined flow rate on actuation of the delivery device, thereby providing for a predetermined residence time of substance in the nasal airway 130.

Figure 9A:
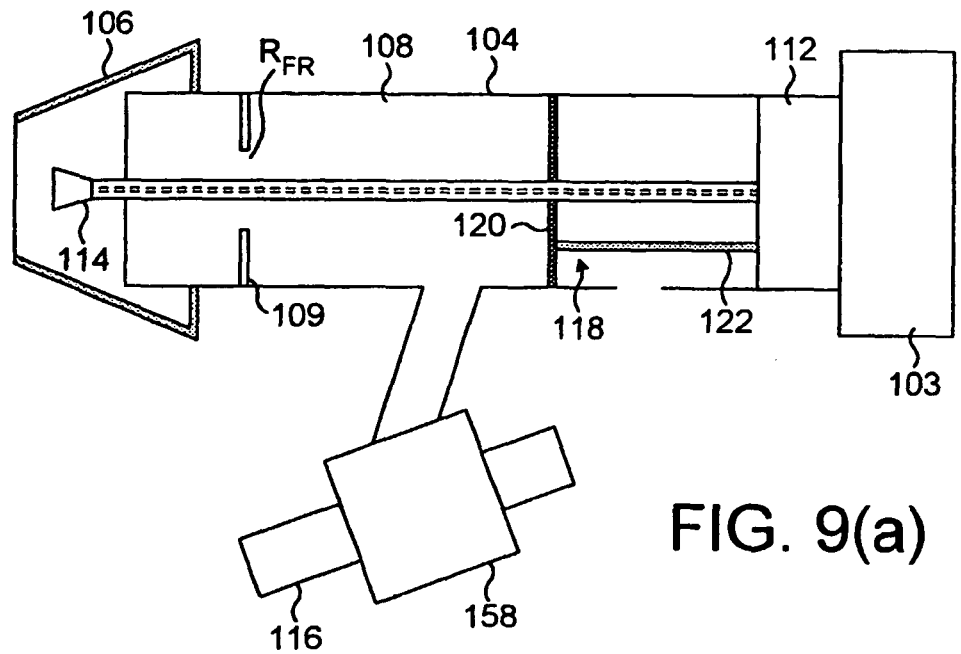
FIG. 9(a) schematically illustrates a nasal delivery device in accordance with a fifth embodiment of the present invention.
Figure 9B:
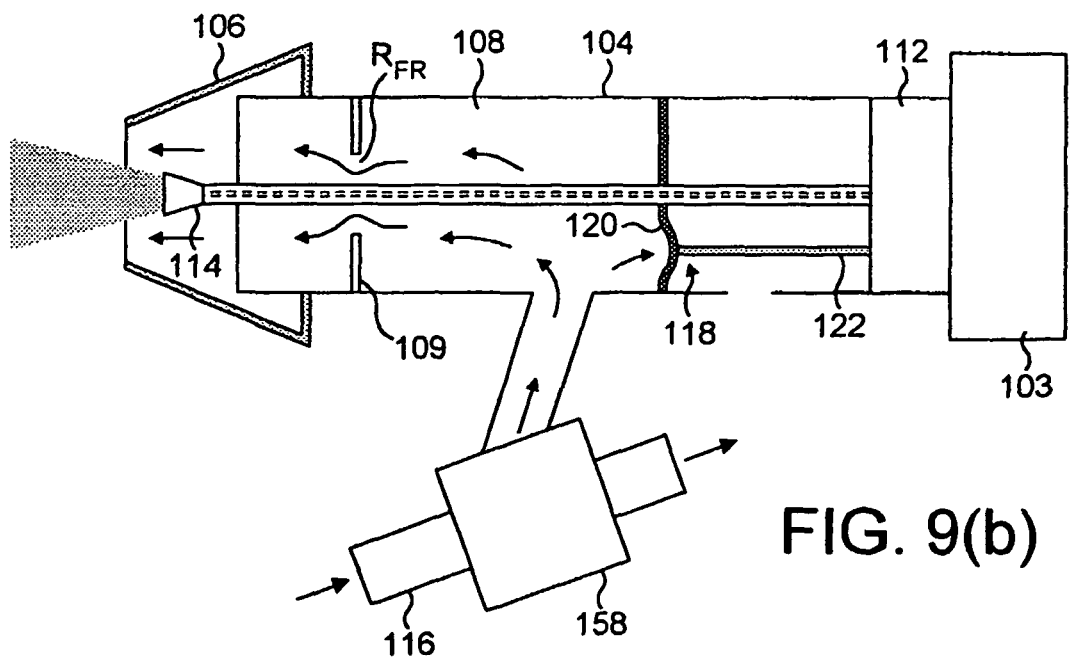
FIG. 9(b) illustrates the nasal delivery device of FIG. 9(a) in the actuated configuration.

FIGS. 9(a) and (b) illustrate a delivery device in accordance with a fifth embodiment of the present invention.

The delivery device of this embodiment is very similar to the delivery device of the above-described fourth embodiment, and thus, in order to avoid unnecessary duplication of description, only the differences will be described in detail, with like reference signs designating like parts The delivery device of this embodiment differs from that of the above-described fourth embodiment in further comprising an exhalation breath actuatable gas delivery unit 158 for delivering a gas flow to the chamber 108 in the housing 104 in response to exhalation by a subject, and in that the mouthpiece 116 is in fluid communication with the gas delivery unit 158 and not the chamber 108 in the housing 104, whereby a gas flow is delivered to the chamber 108 in the housing 104, and hence the nasal airway 130, in response to exhalation through the mouthpiece 116.

Operation of the delivery device is the same as for the above-described fourth embodiment, with a gas flow being delivered to the chamber 108 in the housing 104, and hence a pressure being developed in the nasal airway 130, in response to exhalation through the mouthpiece 116.

FIGS. 10(a) and (b) illustrate a delivery device in accordance with a sixth embodiment of the present invention.

The delivery device of this embodiment is very similar to the delivery device of the above-described fourth embodiment, and thus, in order to avoid unnecessary duplication of description, only the differences will be described in detail, with like reference signs designating like parts The delivery device of this embodiment differs from that of the above-described fourth embodiment in not including a trigger mechanism 118, the substance supply unit 112 instead being actuated by a subject, and in that the nosepiece 106 defines a substance-receiving chamber 160 for receiving an aerosol cloud of substance delivered from the substance supply unit 112 through the nozzle 114. With this configuration, the chamber 160 in the nosepiece 106 functions as a spacer.

Operation of the delivery device is the same as for the above-described fourth embodiment, with the exception that the substance supply unit 112 is actuated manually and, subsequent to actuation, the subject exhales through the mouthpiece 116 to drive an air flow having a predetermined air flow rate, which is determined by the flow resistor 109, through the nosepiece 106 such as to entrain delivered substance and transfer the same into the nasal airway 130.

FIGS. 11(a) to (e) illustrate a nasal delivery device in accordance with a seventh embodiment of the present invention.

The delivery device comprises a housing 232 which includes an air chamber 234 for receiving the exhalation breath of a subject, a nosepiece 240 for fitting in a nostril of a subject which is in fluid communication with the air chamber 234 in the housing 232 and disposed to one, the distal, end of the housing 232, and a mouthpiece 241 through which the subject exhales and which is in fluid communication with the air chamber 234 in the housing 232.

The nosepiece 240 includes a channel 242 through which an air flow is delivered to the nasal airway of a subject.

The delivery device further comprises a channel blocking unit 243 for progressively blocking the channel 242 in the nosepiece 240 in response to an increasing pressure in the air chamber 234 in the housing 232, thereby providing a progressively increasing resistance to an air flow being driven therethrough.

In this embodiment the channel blocking unit 243 comprises a diaphragm 244, in this embodiment a resilient member, which defines a part of the wall of the air chamber 234 in the housing 232, and first and second blocking elements 245, 246, in this embodiment flexible sheet elements, which are guided by respective ones of first and second guides 247, 248 and coupled to respective ones of the blocking elements 245, 246 such as to extend into the channel 242 in the nosepiece 240 on deflection of the diaphragm 244. The diaphragm 244 is configured such as to be progressively deflected with an increasing pressure in the air chamber 234 in the housing 232, such that the blocking elements 245, 246 coupled thereto are progressively extended into the channel 242 in the nosepiece 240 with an increasing pressure in the air chamber 234 in the housing 232, and block the channel 242 in the nosepiece 240 to a predetermined extent on the generation of a pressure in the air chamber 234 in the housing 232 corresponding to the actuation pressure of the substance supply unit 264.

The delivery device further comprises a nozzle 256 for providing an aerosol spray through the nosepiece 240. The nozzle 256 comprises a head 258 which is located, in this embodiment co-axially, within the nosepiece 240, and a delivery tube 262 which is fluidly connected to the head 258.

The delivery device further comprises a substance supply unit 264 for delivering a metered dose of a substance, in this embodiment a metered volume of a liquid containing medicament, either as a suspension or solution, to the nozzle 256.

Figure 11A:
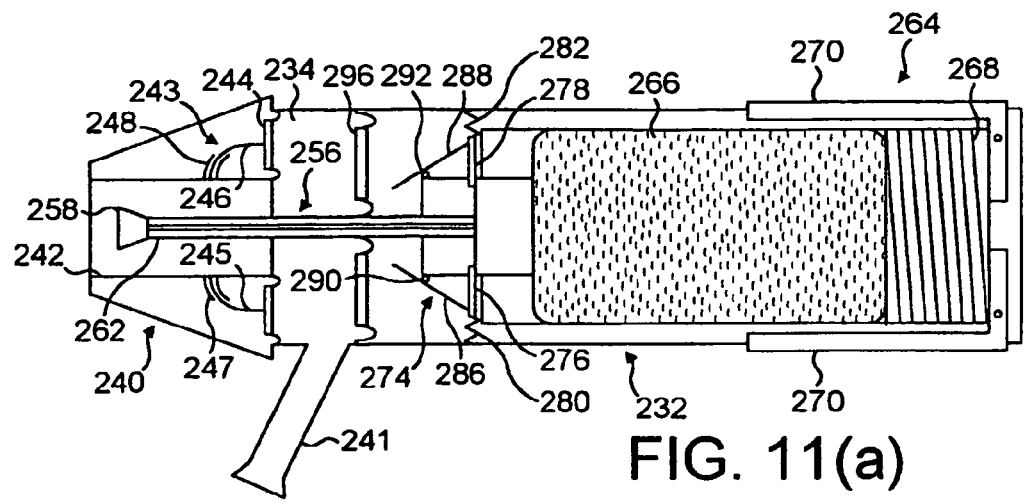
FIG. 11(a) schematically illustrates a nasal delivery device in accordance with a seventh embodiment of the present invention.
Figure 11B:
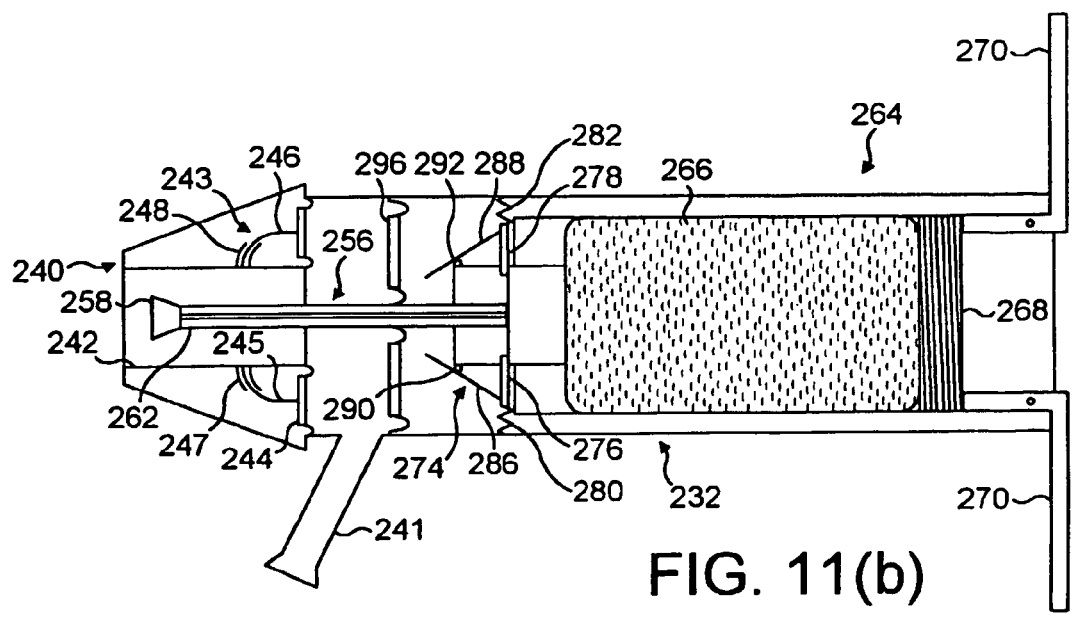
FIG. 11(b) schematically illustrates the nasal delivery device of FIG. 11(a) in a primed, but inoperative configuration.
Figure 11C:
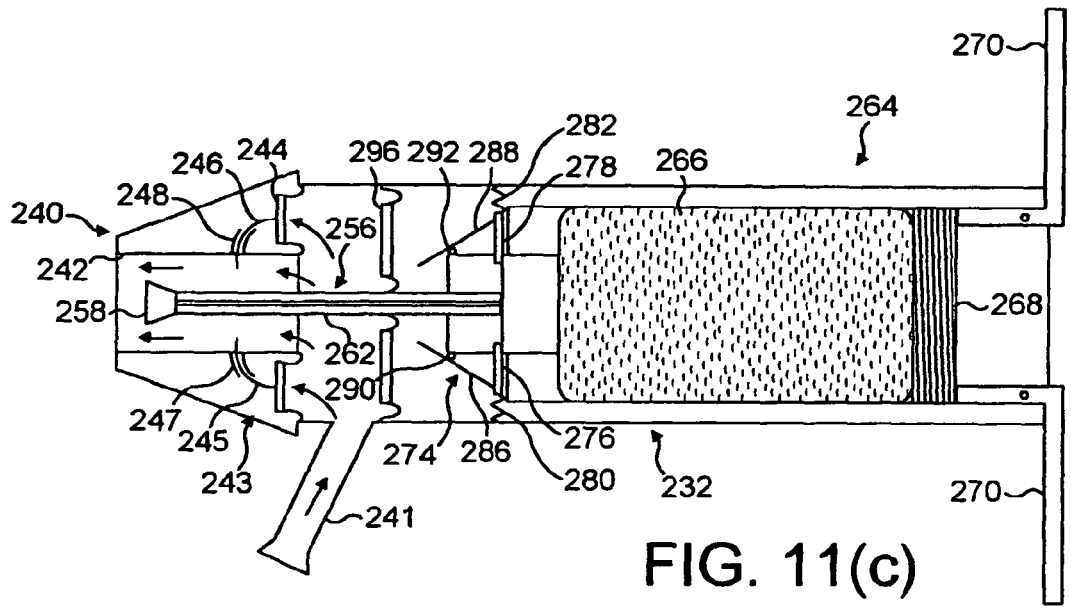
FIG. 11(c) schematically illustrates the nasal delivery device of FIG. 11(a) in an operative configuration.
Figure 11D:
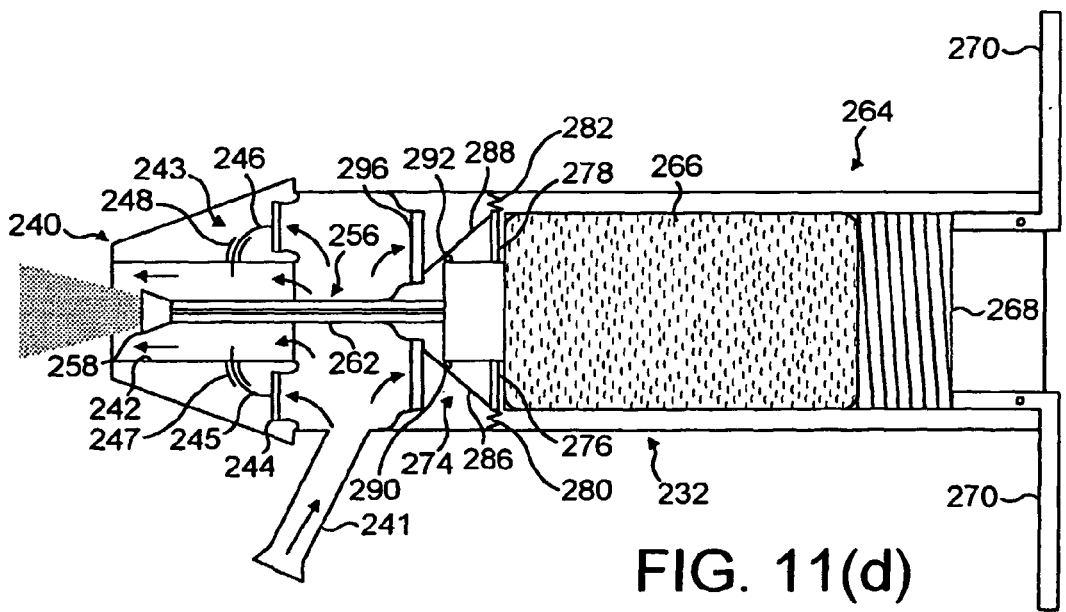
FIG. 11(d) schematically illustrates the nasal delivery device of FIG. 11(a) in an actuated configuration.

In this embodiment the substance supply unit 264 comprises a mechanical delivery pump 266, in particular a spray pump, which is coupled to the nozzle 256 and is configured, on actuation, to deliver a metered dose of a substance, in this embodiment a liquid containing medicament, either as a suspension or solution, as an aerosol spray. The delivery pump 266 is movable relative to the nozzle 256 from a first, non-actuated position (as illustrated in FIGS. 11(a) to (c)) to a second, actuated position (as illustrated in FIG. 11(d)) in which a metered dose of substance has been delivered.

In an alternative embodiment the substance supply unit 264 could comprise an aerosol canister for delivering metered volumes of a propellant, preferably a hydrofluoroalkane (HFA) propellant or the like, containing medicament.

The substance supply unit 264 further comprises a biasing element 268, in this embodiment a resilient element, particularly a compression spring, for biasing the delivery pump 266 in an actuating direction when in the non-actuated position, and a loading member 270, in this embodiment first and second levers, for loading the biasing element 268 such as to bias the delivery pump 266, when in the non-actuated position, with an actuation force. The loading member 270 is movable between a first, rest position in which the biasing element 268 is not loaded thereby, and a second, operative position in which the biasing element 268, when restrained by the delivery pump 266, loads the delivery pump 266 with the actuation force.

The delivery device further comprises a trigger mechanism 274 which is configured to be actuatable to cause the actuation of the substance supply unit 264. In this embodiment the trigger mechanism 274 is configured to be actuatable to cause actuation of the substance supply unit 264 on generation of a predetermined pressure in the air chamber 234 in the housing 232.

The trigger mechanism 274 comprises first and second stop members 276, 278, and first and second biasing elements 280, 282, in this embodiment resilient elements, particularly compression springs, which act to bias respective ones of the first and second stop members 276, 278 inwardly to a stop position (as illustrated in FIGS. 11(a) to (c)) in which the first and second stop members 276, 278 act to prevent movement of the delivery pump 266 from the non-actuated position to the actuated position.

The trigger mechanism 274 further comprises first and second arms 286, 288 which are pivotable about respective pivots 290, 292 and coupled at one end thereof to respective ones of the first and second stop members 276, 278 such that pivoting of the arms 286, 288 to a release position causes the respective ones of the stop members 276, 278 to which the arms 286, 288 are coupled to be moved outwardly against the bias of the first and second biasing elements 280, 282 to a release position (as illustrated in FIG. 11(d)) in which the stop members 276, 278 are disposed outwardly of the head of the delivery pump 266, such that the delivery pump 266, when biased by the biasing element 268, is driven to the actuated position. In being driven to the actuated position, a metered dose of a substance is delivered from the nozzle 256 as an aerosol spray.

The trigger mechanism 274 further comprises a diaphragm 296, in this embodiment a resilient member, which defines a part of the wall of the air chamber 234 in the housing 232. The diaphragm 296 is configured such as, on generation of a predetermined actuation pressure within the air chamber 234 in the housing 232, to be deflected such as to engage the other, distal ends of the arms 286, 288 and cause the same to be pivoted to the release position. At this actuation pressure, the blocking elements 245, 246 of the channel blocking unit 243 block the channel 242 in the nosepiece 240 to a predetermined extent such that the flow rate of an air flow driven therethrough is at a predetermined value on actuation.

With this configuration, the flow rate of exhaled air from an exhalation breath of a user decreases progressively as the pressure in the air chamber 234 in the housing 232 increases to a predetermined flow rate at a pressure corresponding to the actuation pressure of the substance supply unit 264.

Figure 12A:
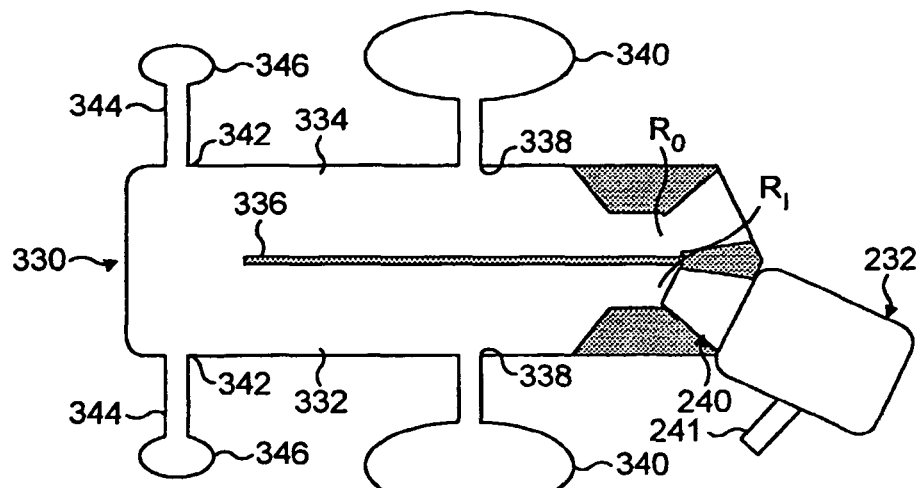
FIG. 12(a) illustrates the nasal delivery device of the seventh embodiment of the present invention fitted to a nostril of a subject, where the subject is not exhaling through the mouthpiece of the delivery unit.
Figure 12B:
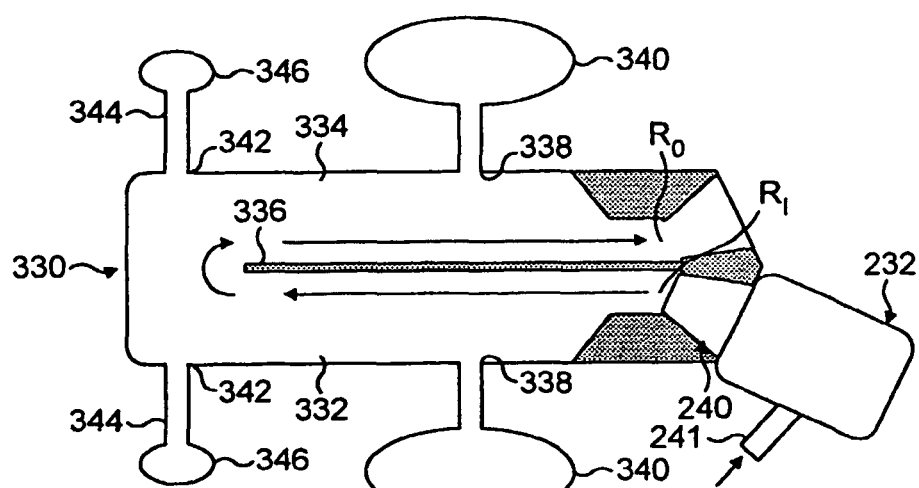
FIG. 12(b) illustrates the nasal delivery device of the seventh embodiment of the present invention fitted to a nostril of a subject, where the delivery device has been actuated and the subject is continuing to exhale through the mouthpiece of the delivery device.

Operation of the delivery device will now be described hereinbelow with reference to FIGS. 12(a) and (b), which drawings diagrammatically illustrate the nasal airway 330 of a human subject. The nasal airway 330 comprises the two nasal cavities 332, 334 separated by the nasal septum 336, which airway 330 includes numerous ostia, such as the paranasal sinus ostia 338 connected to the paranasal sinuses 340 and the tubal ostia 342 connected to the tuba auditiva 344 and the middle ears 346, and olfactory cells, and is lined by the nasal mucosa.

Firstly, the substance supply unit 264 is primed by operating the loading members 270 to load the biasing element 268. The nosepiece 240 of the delivery device is then inserted in one nostril of a subject. The subject then begins to exhale through the mouthpiece 241, which exhalation acts to close the oropharyngeal velum of the subject and increase the pressure in the air chamber 234 in the housing 232, and hence the nasal airway 330, by the introduction of exhaled air from the exhalation breath thereinto. With this increasing pressure in the air chamber 234 in the housing 232, the diaphragm 244 of the channel blocking unit 243 is progressively deflected and the blocking elements 245, 246 of the channel locking unit 243 coupled thereto are progressively extended into the channel 242 in the nosepiece 240. Also with this increasing pressure in the air chamber 234 in the housing 232, the diaphragm 296 of the trigger mechanism 274 is progressively deflected. When the pressure in the air chamber 234 in the housing 232 reaches the actuation pressure of the substance supply unit 264, the diaphragm 296 of the trigger mechanism 274 is deflected such as to engage the other, distal ends of the arms 286, 288 of the trigger mechanism and cause the same to be pivoted to the release position, whereby the trigger mechanism 274 is actuated and enables actuation of the substance supply unit 264. At this actuation pressure, the blocking elements 245, 246 of the channel blocking unit 243 block the channel 242 in the nosepiece 240 to a predetermined extent such that the flow rate of an air flow driven therethrough is at a predetermined value on actuation.

A yet further advantage is that the air flow acts to create a positive pressure inside the nasal cavities connected in series, which tends to expand and widen narrow and congested regions.

A further advantage is that the nosepiece 6 of the delivery unit 1 acts to expand the narrowest, anterior part of the nasal cavity 32 to which substance is delivered, and thereby reduces the unwanted high deposition in the anterior region of the nasal cavity 32 which is lined by squamous epithelium.

Finally, it will be understood that the present invention has been described in its preferred embodiments and can be modified in many different ways without departing from the scope of the invention as defined by the appended claims.

For example, in one modification, the flow resistor unit 2 of the above-described first and second embodiments could comprise an electrically-operable progressive resistor 28 such as to provide for a flow resistance having a predeterminable profile.

In addition, in another modification, and particularly through the use of an electrically-operable progressive resistor 28, the substance supply unit 12 could be operable in response to an input from the flow resistor unit 2.

The invention claimed is:

1. A nasal delivery device for delivering a substance to a nasal cavity of a subject, comprising:
   a delivery unit configured to deliver a flow entraining a substance to one nostril of a subject, around the nasal septum, and out the other nostril of the subject, the delivery unit including (i) a nosepiece adapted to fit the one nostril of the subject and (ii) a mouthpiece configured to cause substantial closure of the subject's oropharyngeal velum when the subject exhales through the mouthpiece; and
   a flow resistor unit adapted to fit to the other nostril of the subject, the flow resistor unit including a progressive resistor configured to progressively provide an increasing flow resistance to the delivered flow when the device is in use by the subject.

2. The delivery device of claim 1, wherein the progressive resistor comprises an inflatable member which provides a progressively increasing resistance to the delivered flow.

3. The delivery device of claim 1, wherein the flow resistor unit includes a movable member which is movable under the action of a pressure developed in the nasal airway, and a biasing element for providing a progressively increasing resistance to the movement of the movable member.

4. The delivery device of claim 3, wherein the flow resistor unit further includes a housing in which the movable member is movable, the housing including an aperture therein which is located such as to vent the housing when movable member is driven a predeterminable distance corresponding to a first predeterminable pressure, whereby the flow resistance decreases and the flow rate increases following the development of a second predeterminable pressure.

5. The delivery device of claim 4, wherein the flow resistor unit includes a filter for collecting any vented material.

6. The delivery device of claim 1, wherein the delivery unit includes a substance supply unit which is actuatable to supply a substance.

7. The delivery device of claim 6, wherein the substance supply unit is configured to be actuatable by the flow resistor unit.

8. The delivery device of claim 6, wherein the substance supply unit is configured to be actuatable to supply a substance on generation of a predetermined pressure within the device.

9. The delivery device of claim 6, wherein the substance supply unit is configured to be actuatable to supply a substance at a predetermined flow rate.

10. The delivery device of claim 6, wherein the substance supply unit is configured to be actuatable to supply a substance on generation of a predetermined pressure within the device and at a predetermined flow rate.

11. The delivery device of claim 1, wherein the delivery unit further includes a flow channel fluidly connected to the nosepiece through which a gas flow, separate to an exhaled air flow from an exhalation breath of the subject, is in use delivered, and a gas supply unit for supplying a gas flow to the flow channel.

12. The delivery device of claim 1, wherein the substance supply unit includes a dosing unit for supplying a substance.

13. The delivery device of claim 12, wherein the dosing unit comprises a nebulizer for supplying an aerosol.

14. The delivery device of claim 12, wherein the dosing unit comprises an aerosol canister for supplying an aerosol.

15. The delivery device of claim 12, wherein the dosing unit comprises a delivery pump unit for supplying an aerosol.

16. The delivery device of claim 15, wherein the dosing unit comprises a liquid pump unit for supplying a liquid aerosol.

17. The delivery device of claim 15, wherein the dosing unit comprises a powder pump unit for supplying a powder aerosol.

18. The delivery device of claim 12, wherein the dosing unit comprises a powder delivery unit for delivering a powder aerosol.

19. A nasal delivery device for delivering a substance to a nasal cavity of a subject, comprising:
   a delivery unit for delivering a flow entraining a substance to one nostril of a subject, the delivery unit including a mouthpiece through which the subject in use exhales, a nosepiece for fitting to the one nostril of the subject and a flow channel fluidly connecting the nosepiece and the mouthpiece, whereby exhaled air from an exhalation breath is delivered through the nosepiece; and
   a flow resistor unit for fitting to the other nostril of the subject, the flow resistor unit including a progressive resistor for progressively providing an increasing flow resistance to the delivered flow.

20. A method of delivering a substance to a nasal cavity of a subject, comprising the steps of:
   exhaling through a mouthpiece configured to cause substantial closure of the subject's oropharyngeal velum when the subject exhales through the mouthpiece;
   delivering a flow entraining a substance to one nostril of a subject, around the nasal septum, and out the other nostril of the subject; and
   progressively providing an increasing flow resistance to the delivered flow.

21. The method of claim 20, further comprising the step of:
   decreasing the flow resistance on development of a predeterminable pressure.

22. The method of claim 20, wherein the step of progressively providing an increasing flow resistance to the delivered flow is accomplished by fitting a flow resistor unit to the other nostril of the subject, the flow resistor unit including a progressive resistor for progressively providing an increasing flow resistance to the delivered flow.

23. A method of delivering a substance to a nasal cavity of a subject, comprising the steps of:
   providing a mouthpiece through which the subject exhales;
   providing a nosepiece to one nostril of the subject, the nosepiece being fluidly connected to the mouthpiece, whereby exhaled air from an exhalation breath is delivered through the nosepiece;
   the subject exhaling through the mouthpiece to deliver an air flow entraining a substance through the nosepiece to the one nostril of the subject; and
   progressively providing an increasing flow resistance to the delivered flow.

24. A nasal delivery device for delivering a substance to a nasal cavity of a subject, comprising:
   a delivery unit configured to deliver a flow entraining a substance to one nostril of a subject, around the nasal septum, and out the other nostril of the subject, the delivery unit including (i) a nosepiece adapted to fit the one nostril and (ii) a mouthpiece configured to cause substantial closure of the subject's oropharyngeal velum when the subject exhales through the mouthpiece; and a flow resistor unit adapted to fit to the other nostril of the subject, the flow resistor unit including a progressive resistor configured to progressively provide an increasing flow resistance to the delivered flow.

25. The nasal delivery device of claim 24, wherein the delivery unit further includes a flow channel fluidly connecting the nosepiece and the mouthpiece.

26. A nasal delivery device for delivering a substance to a nasal cavity of a subject, comprising:

a delivery unit configured to deliver a flow entraining a substance to one nostril of a subject, around the nasal septum, and out the other nostril of the subject, the delivery unit including (i) a nosepiece adapted to fit the one nostril of the subject and (ii) a mouthpiece configured to cause substantial closure of the subject's oropharyngeal velum when the subject exhales through the mouthpiece; and a flow resistor unit adapted to fit to the other nostril of the subject, the flow resistor unit including means for progressively providing an increasing flow resistance to the delivered flow.

27. The nasal delivery device of claim 26, wherein the delivery unit further includes flow channel fluidly connecting the nosepiece and the mouthpiece.

28. A method of delivering a substance to a nasal cavity of a subject, comprising the steps of:

providing a delivery unit configured to deliver a flow entraining a substance to one nostril of a subject, around the nasal septum, and out the other nostril of the subject, the delivery unit including (i) a nosepiece adapted to fit the one nostril and (ii) a mouthpiece configured such that when the subject exhales through the mouthpiece, the mouthpiece causes substantial closure of the subject's oropharyngeal velum;

providing a flow resistor unit adapted to fit to the other nostril of the subject, the flow resistor unit including a progressive resistor configured to progressively provide an increasing flow resistance to the delivered flow; and delivering the substance to the nasal cavity of a subject using the delivery unit and the flow resistor.

29. The method of claim 28, wherein the delivery unit further includes a flow channel fluidly connecting the nosepiece and the mouthpiece.

* * * * *